United States Patent [19]

Yamashina

[11] Patent Number: 4,851,357
[45] Date of Patent: Jul. 25, 1989

[54] PLATES FOR ASSAY OF SUGAR CHAINDIRECTED ANTIBODY AND PRODUCTION THEREOF

[76] Inventor: Ikuo Yamashina, 2, Shimogamohigashimorimae-cho, Sakyo-ku, Kyoto-shi, Kyoto, Japan

[21] Appl. No.: 25,103

[22] Filed: Mar. 12, 1987

[30] Foreign Application Priority Data

Mar. 14, 1986 [JP] Japan .................. 61-57772

[51] Int. Cl.$^4$ ............................ G01N 33/544
[52] U.S. Cl. ........................ 436/528; 436/822; 436/827
[58] Field of Search .......... 436/528, 827, 822

[56] References Cited

U.S. PATENT DOCUMENTS

| | | | |
|---|---|---|---|
| 4,067,959 | 1/1978 | Bolz . | |
| 4,075,194 | 2/1978 | Sela | 436/528 X |
| 4,407,965 | 10/1983 | Yanaihara | 436/822 X |
| 4,410,634 | 10/1983 | Cooper et al. . | |
| 4,493,793 | 1/1985 | Chu | 436/528 X |
| 4,571,382 | 2/1986 | Adachi | 436/827 X |
| 4,607,009 | 8/1986 | Steplewski | 436/528 X |
| 4,623,629 | 11/1986 | Kerschensteiner | 436/528 X |
| 4,675,287 | 6/1987 | Reisfeld | 436/528 X |

FOREIGN PATENT DOCUMENTS

0131546 1/1985 European Pat. Off. .

OTHER PUBLICATIONS

Liebert et al., "Journal of Immunological Methods", 85, pp. 97–104 (1985).
Metzgar et al., "Proc. Natl. Acad. Sci. U.S.A.", vol. 81, pp. 5242–5246, Aug. 1984.
Rice et al., Chemical Abstracts 99:51537g, p. 381 (1983).
Perrin et al., Chemical Abstracts 105:77142s, (1986).
Delpech et al., Chemical Abstracts 103:119095v, p. 349 (1985).

*Primary Examiner*—Barry S. Richman
*Assistant Examiner*—Jill Johnston
*Attorney, Agent, or Firm*—Birch, Stewart, Kolasch & Birch

[57] ABSTRACT

The invention relates to an assay plate for a sugar chain-directed antibody on which a mucin-type glycopeptide is fixed in a solid phase in the presence of an alkylenedialdehyde and a basic poly-peptide or basic synthetic polymer. The invention also relates to an assay plate wherein a serum-type glycopeptide is fixed in a solid phase by acylation with a higher fatty acid, which makes an assay fo sugar chain-directed antibody possible. Moreover, the invention makes the preparation of a hybridoma producing sugar chain-directed antibody possible, and relates to a process for the production thereof.

17 Claims, 1 Drawing Sheet

PLATES FOR ASSAY OF SUGAR CHAIN DIRECTED ANTIBODY AND PRODUCTION THEREOF

BACKGROUND OF THE INVENTION

1. Field of the Invention

The present invention relates to an assay plate for detecting an antibody specific to the sugar chain of complex carbohydrates. By using this plate, a hybridoma which produces a monoclonal antibody specific to a sugar chain can be efficiently selected.

2. Prior Art

In general, it is said that it is difficult to prepare an antibody specific to the sugar chain of complex carbohydrates such as those of glycoproteins, glycolipids and proteoglycans widely distributed in nature, though many attempts have been made. Most of the antibodies prepared until now are directed to a variety of blood group substances such as A, B, H, Le$^a$, Le$^b$, I, etc. These antibodies are valuable in a sense but they are nearly useless, for example, in the recognition of cancer-associated changes on cell surface membranes. It has been expected that the sugar chain of complex carbohydrates on the surface of cells might be changed accompanied with malignant transformations of cells. This change is multifarious, so that the preparation of a variety of antibodies specific to the sugar chain has been desired strongly. Under this situation, an assay of the antibody titer in serum has been carried out as follows: the intact or formaldehyde-treated cells or the complex carbohydrates isolated from the cells are administered singly or together with an adjuvant intravenously, intraperitoneally, subcutaneously or intracutaneously to an animal for immunization, and the antibody titer in the serum is determined by means of the binding ability as an index between the serum antibody and the cells used in immunization or their modified product.

In the aforementioned assay, it was practically impossible to select the antibody specific to the sugar chain out of antibodies abundant in serum since most of the antibodies have specificity to the protein components on the cell surface.

The object of the present invention is to provide an assay plate by which only the titer of the antibody specific to the sugar chain can be determined out of a variety of serum antibodies, and consequently it leads to isolation of a clone which is capable of producing an antibody specific to the sugar chain.

SUMMARY

Figure 1:
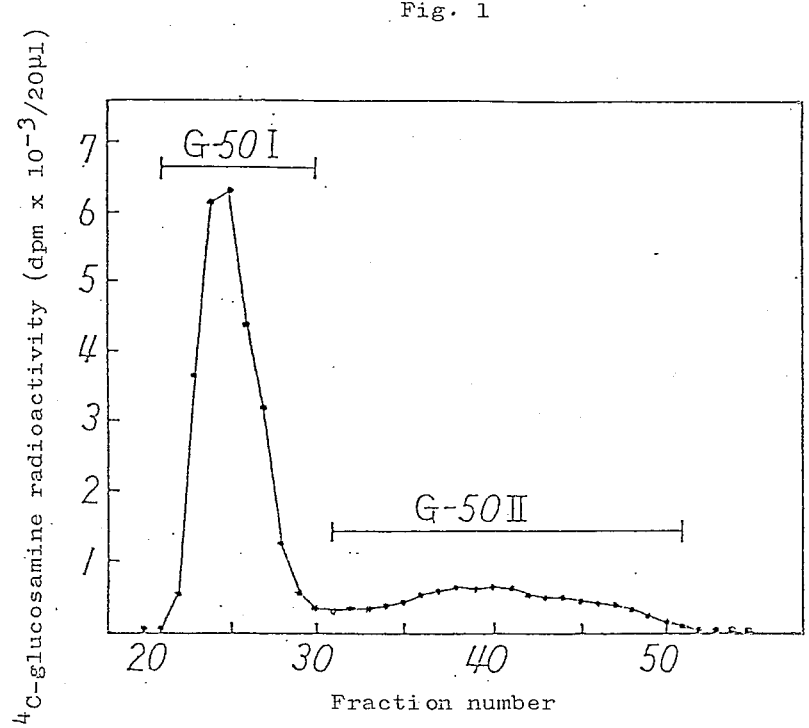
FIG. 1 shows a result of the isolation of a glycopeptide used in this invention through the relation between fraction number and $^{14}$C-glucosamine radioactivity.

The invention provides an assay plate for a sugar chain-directed antibody on which a mucin-type glycopeptide is fixed in a solid phase in the presence of an alkylenedialdehyde and a basic polypeptide or a basic synthetic polymer. The invention also provides an assay plate for sugar chain-directed antibody on which a serum-type glycopeptide is fixed in a solid phase by acylation with a higher fatty acid, and a process for production thereof.

The use of the plate immobilizing glycopeptide or glycoprotein makes an assay of a sugar chain-directed antibody possible. This makes the preparation of hybridoma producing sugar chain-directed antibody also possible.

DETAILED DESCRIPTION OF THE INVENTION

The invention provides an assay plate for a sugar chain-directed antibody on which a mucin-type glycopeptide is fixed in a solid phase in the presence of an alkylenedialdehyde and a basic polypeptide or basic synthetic polymer. The invention also provides an assay plate for a sugar chain-directed antibody on which a serum-type glycopeptide is fixed in a solid phase by acylation with a higher fatty acid, and a process for the production thereof.

In preparing the assay plates of the present invention, animal cells, specimens therefrom or glycoproteins which are isolated are digested thoroughly with protease or the like in order to remove the peptide portion as much as possible. The resulting glycopeptide is adsorbed and solidified on an assay plate for an antigen-antibody reaction.

By using the assay plates of the present invention, it is possible to detect a sugar chain-directed antibody and assay the titer of the antibody, to select an antibody-producing hybridoma, and isolate a clone which produces a sugar chain-directed antibody.

In the detection and assay of the sugar chain-directed antibody the sugar chain is prepared in the form of a glycopeptide and adsorbed on a plate, to which for example a serum or cell-culture broth to be assayed is added, and then a secondary antibody or protein A (e.g. product of Nakarai Chemical Co., Ltd.) specific to the primary antibody is added. As an indicator the secondary antibody or protein A previously labelled with a radioactive isotope or with an enzyme that can be readily assayed is employed.

In the present invention, tumor cells or a variety of mucintype glycoproteins are used as sources of glycopeptide. The method is naturally applicable to any kind of animal and plant cells, microorganism cells, and a variety of glycoproteins isolated therefrom.

In preparing the glycopeptides, non-specific proteinase isolated from Streptomyces griseus, for example, Pronase P (product of Kaken Seiyaku Co., Ltd.), or their equivalent proteolytic enzymes may be employed. This digestion is made thoroughly in order to eliminate amino acids from the glycoprotein as much as possible.

Sephadex G-25 (Pharmacia AB) which is used in the fractionation of the glycopeptides may be used in a form of usual particle size or the so-called "fine" grade. Other equally effective adsorbents such as Biogel P-4 or P-6 (made by Bio-Rad Co.; USA) may also be employed. In place of Sephadex G-50, Biogel P-6 or P-10 may be used equivalently. The size of column may be determined according to the amount of the sample to be applied, for example, when about 10 ml of sample is used, a column of 1.3×60 cm may be employed.

The orcinol-sulfuric acid reaction is utilized as a convenient method for quantitative analysis of neutral sugars (e.g. galactose, mannose) which usually constitute sugar component of glycopeptides. In the case of using a relatively small quantity of cells at the start, the culture may be carried out in a medium containing an isotope-labelled monosaccharide (usually $^3$H— or $^{14}$C—labelled glucosamine), whereby the sugar chain portion of the glycopeptide is labelled metabolically and utilized in monitoring the eluate from the column.

The two fractions obtained by separation with Sephadex G-50 can be used as a test antigen without further purification. However, in order to use them for the determination of the epitopic structure, they need to be further purified by means of gel filtration on Sephadex G-200 or another equivalent gel-filtration material. The mucopolysaccharide contained in mucin-type glycopeptide fraction has no influence on the preparation of the assay plate.

As for a plate used for the solid phase assay, synthetic resins, celluloses, glass plates, wood pieces, textiles, paper sheets, and the like may be employed. The synthetic resins include for example polyethylene, polypropylene, polybutadiene, polystyrene, poly(vinyl chloride), methyl polymethacrylate, polyacrylonitrile, poly(vinyl alcohol), polyesters, polyamides, polyurethanes, polyethers, nylon, and the like, and their functional derivatives to which an amino group, carboxyl group, etc. have been introduced. The celluloses mean cellulose, cellulose acetate, ethylcellulose, cellulose nitrate, and the like. Particularly, a microtiter plate made of poly(vinyl chloride) [Costar 2595 (Costar Co., Ltd., USA)] is very convenient.

The mucin-type glycopeptide may be adsorbed on the plate by way of an alkylenedialdehyde and a basic polypeptide or basic synthetic polymer. The preferred alkylenedialdehyde used is represented by the general formula:

$$OHC(CH_2)_nCHO$$

(wherein n indicates an integer of 1–8. Particularly, the dialdehydes wherein n is 2–5 is, more preferred particularly and, glutaraldehyde is preferably used. As for the basic polypeptide, polylysine is preferably used. The basic synthetic polymer means those of which the polymer chain contains an amino or imino group or groups, for example, vinylpyridine polymer, vinylamine polymer.

Among the aforementioned reagents to make the solid phase, glutaraldehyde and polylysine have been utilized in adsorbing cells on the plate [e.g., R.S. Metzgar et al., Proc. Natl. Acad. Sci., 81, 5242–5246 (1984)]. The application of these reagents to the glycopeptide is one of the characteristics of the present invention. In this adsorptive reaction, it is presumed that a bridge by the Schiff base is formed between the amino group of glycopeptide and that of the polylysine through the glutaraldehyde, and the resulting bond can be converted into a more stable bond by reduction with a reducing agent, e.g., sodium borohydride ($NaBH_4$). In the procedure under a neutral condition, stabilization by the reduction is not always necessary.

In order to make the serum-type glycopeptide adsorb on a plate, it is necessary to give lipophilicity to the glycopeptide. In this invention, the lipophilicity can be afforded by binding of higher fatty acids, for example, saturated fatty acids such as lauric acid, myristic acid, palmitic acid, stearic acid, arachidic acid, behenic acid, lignoserinic acid, etc., or unsaturated fatty acids such as oleic acid, linolic acid, linolenic acid, arachidonic acid. The binding of these fatty acids to the glycopeptide may be achieved by means of a conventional acylation method, for example, method using a condensing agent, e.g., dicyclohexylcarbodiimide (DCC), method using acid anhydrides, method using acid halides, active ester method, etc. In making the lipophilic glycopeptide to be adsorbed on the plate, the glycopeptide is dissolved in an appropriate solvent, e.g., pyridine, dimethylformamide, to which if required water is added, and the aforementioned plate is treated therewith. The resulting plate on which the glycopeptide is adsorbed is if required dried under reduced pressure in the presence of a drying agent, e.g., phosphorus pentoxide or calcium oxide.

The use of the plate immobilizing glycopeptide or glycoprotein makes an assay of a sugar chain-directed antibody possible, moreover, which makes the preparation of a hybridoma producing sugar chain-directed antibody also possible.

EXAMPLE

The invention will be explained in more detail by the following working examples and additional pertinent examples, by which however the scope of the present invention is not limited.

Pertinent Example 1

Preparation of Glycopeptide from Tumor Cells

Established cell line of human intestinal cancer (SW1116, LS180, HCT8, etc. obtained from ATCC) was incubated in a Dalbecco medium containing 10% fetal calf serum. The harvesting cells were washed repeatedly with a phosphate-buffered aqueous sodium chloride solution (hereinafter abbreviated to as PBS; containing 138 mM sodium chloride, 2.7 mM potassium chloride, 8.1 mM sodium monohydrogenphosphate, 1.5 mM potassium dihydrogenphosphate, 1.0 mM calcium chloride, and 0.5 mM magnesium chloride; pH 7.4), then PBS containing 1% Triton X-100 (Rohm & Haas, Co.) was added, and the mixture was stirred under ice cooling, and submitted to centrifugation. The supernatant was applied to dialysis and then to lyophilization. The lyophilizate was defatted well with a mixture of chloroform and methanol (2:1 by volume) and suspended in an acetate buffer containing 0.01M calcium acetate, to which was then added 1/50 part (by weight for the lyophilizate) of Pronase P (Kaken Seiyaku Co., Ltd.), and the mixture was allowed to stand for protein digestion at 37° C. for 3 days, during which time a small amount of toluene was added for the purpose of preservation. To the digest which almost became colorless was added the same volume of 10% trichloroacetic acid and resulting precipitate was removed by centrifugation. For the purpose of removing trichloroacetic acid from the resulting supernatant containing glycopeptide, the supernatant was well mixed with the same volume of ethylether and the mixture was centrifuged to remove the ether phase. This ether extraction was repeated about 3 times and it was confirmed that the water phase became about pH 5. Then, the mixture was applied to a column of Sephadex G-25 previously equilibrated with 0.5 M pyridine-acetic acid buffer (pH 5.0) and developed with the same buffer solution. Eluates were collected by a fraction collector and the fractions positive in the orcinol-sulfuric acid reaction were collected and lyophilized. The lyophilizate was dissolved in 0.5 M pyridine-acetic acid buffer (pH 5.0). The mixture was subjected to gel filtration using Sephadex G-50 and fractionated to 5 ml-portions by a fraction collector (FIG. 1). This fractionation gave fractions (G-50-I) passing through the G-50 column and fractions (G-50-II) eluted later therefrom. Usually, the former contains glycopeptide derived from glycoprotein of mucin-type (O-glycoside type) and the latter contains glycopeptide derived from glycoprotein of serum-type (N-glycoside type). FIG. 1 proves what is mentioned above through the relation between the fraction number (abscissa) and $^{14}C$-labelled glucosamine radioactivity (dpm×$10^{-3}$/20 μl, ordinate).

The fractions of numbers 20-29 were collected and lyophilized. The resultant was applied to gel filtration using Sephadex G-200 to give mucin-type glycopeptide without serum-type one.

PERTINENT EXAMPLE 2

Preparation of Mucin-Type Glycoprotein from Glandula Submandibularis

Preparation of mucin-type glycoprotein from glandula submandibularis of a cow, a pig, a sheep and the like was performed according to the method described in papers, namely, G. Tettamanti et al., Arch. Biochem. Biophys. 124, 41-50, 1968 in the case of a cow and a sheep and M. DeSalegui et al., Arch. Biochem. Biophys. 129, 49-56, 1969 in the case of a pig.

Glycopeptides can be prepared from these glycoproteins by Pronase digestion. However, glycoproteins are more preferably used in adsorption on a plate as noted later than glycopeptides and so it is not always necessary to prepare glycopeptides.

EXAMPLE 1

Adsorption of Mucin-Type Glycopeptide or Glycoprotein on a Plate

Mucin-type glycopeptide derived from a cell is adsorbed on a plate as follows.

In 1 ml of water is dissolved 1 mg of mucin-type glycopeptide. The following solution is prepared as a reagent for adsorption.

Solution I: PBS containing 0.9% sodium chloride and 0.02% sodium azide,

Solution II: PBS containing 0.25% glutaraldehyde and

Solution III: PBS containing 0.25 mg of polylysine (Sigma P1274, average molecular weight 90,000) per 1 ml of PBS For adsorption on a plate, 100 μl of mucin-type glycopeptide is mixed with 1.9 ml of the above solution I and 33 μl of the above solution II and 20μl of this mixture is distributed to each well of a 96-well poly(vinyl chloride) microtiter plate and allowed to stand at room temperature for about 1 hr. Then, 10 μl of the above solution III is poured into the each well and the mixture in the well is quickly stirred by shaking the plate and allowed to stand at 4° C. for 2 days. In accordance with the above method, about 50% of glycopeptide is adsorbed on a plate.

Adsorption of mucin-type glycoprotein on a plate was achieved in the same manner as for mucin-type glycopeptide derived from a cell except for the use of a solution containing 1 mg/ml of mucintype glycoprotein prepared from glandula submandibularis of a cow, a pig, a sheep and the like in water. Mucin-type glycoprotein was adsorbed to a considerable extent on a plate even in the case for which only polylysine but not glutaraldehyde is used as adsorbent and, moreover, even in the case for which no adsorbent is used. However, the highest amounts of glycoproteins were adsorbed on a plate in the case for which both glutaraldehyde and polylysine were used.

EXAMPLE 2

Adsorption of Serum-type Glycopeptide on a Plate

Glycopeptide prepared from serum-type glycoprotein derived from a cell or other living material is adsorbed on a plate by the following method.

To 2.5 mg of serum-type glycopeptide in 80μl of water is added 200 μl of pyridine and then added 9.915 mg of palmitic acid anhydride in 1 ml of pyridine. The mixture is stirred and allowed to react at 37° C. for 6 hr. The resulting mixture is dried out with a rotary evaporator, washed with ether and again dried out to give dried palmitoyl glycopeptide (hereinafter abbreviated to as pal-GP). To pal-GP corresponding to 2.5 mg of glycopeptide in 2.04 ml of 98% pyridine is added 1.837 ml of water. To each well of a microtiter plate is distributed 20 μl of the mixture. The plate is dried out in the presence of phosphorus pentoxide in a desiccator, washed 3 times with PBS containing 1% bovine serum albumin (1% BSA) to remove glycopeptide not adsorbed and again dried out. According to this method about 10% of glycopeptide is adsorbed on a plate.

PERTINENT EXAMPLE 3

Detection and Titration of Sugar Chain-Directed Antibody

An immunized serum prepared by administering cells or glycoprotein standard preparation to mouse or the like is diluted with PBS containing 0.1% BSA and 0.02% sodium azide, 20μl of which is placed on a plate with glycopeptide adsorbed and allowed to stand overnight at 4° C. Then, the plate is washed with PBS containing 1% BSA. PBS (50μl) containing $^{125}I$-labelled protein A ($10^5$ cpm) is added to the plate, which is allowed to stand at room temperature for 2 hr. The plate is repeatedly washed with 150 μl of PBS. After the radioactivity of the washing disappears, the radioactivity of the plate is measured.

What we claim is:

1. A plate for an assay of a sugar chain-directed antibody which is produced by fixing a glycopeptide prepared from tumor cells or mucin glycoproteins on a plate in the presence of an alkylenedialdehyde and a basic polypeptide or a basic synthetic polymer.

2. The plate for an assay of a sugar chain-directed antibody claimed in claim 1, wherein the alkylenedialdehyde is represented by the formula:

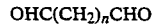

$OHC(CH_2)_nCHO$ wherein n is an integer of 1-8.

3. The plate for an assay of a sugar chain-directed antibody claimed in claim 1, wherein the alkylenedialdehyde is glutaraldehyde.

4. The plate for an assay of a sugar chain-directed antibody claimed in claim 1, wherein the basic polypeptide is polylysine.

5. The plate for an assay of a sugar chain-directed antibody claimed in claim 1, wherein the basic synthetic polymer contains an amino group or an imino group.

6. A process for producing a plate for an assay of a sugar chain-directed antibody which comprises fixing a glycopeptide prepared from tumor cells or mucin glycoproteins on a fixing plate in the presence of an alkylenedialdehyde and a basic polypeptide or a basic synthetic polymer.

7. the process for producing a plate for an assay of a sugar chain-directed antibody claimed in claim 6, wherein the alkylenedialdehyde is represented by the formula:

$$OHC(CH_2)_nCHO$$

wherein n is an integer of 1-8.

8. The process for producing a plate for an assay of a sugar chain-directed antibody claimed in claim 6, wherein the alkylenedialdehyde is glutaraldehyde.

9. The process for producing a plate for an assay of a sugar chain-directed antibody claimed in claim 6, wherein the basic polypeptide is polylysine.

10. The process for producing a plate for an assay of a sugar chain-directed antibody claimed in claim 6, wherein the fixing plate is of synthetic resin, cellulose, glass, wood pieces, textile or paper.

11. A plate for an assay of a sugar chain-directed antibody which is produced by fixing a glycopeptide prepared from tumor cells or serum glycoproteins on a plate by acylation with a higher fatty acid.

12. The plate for an assay of a sugar chain-directed antibody claimed in claim 11, wherein the higher fatty acid is palmitic acid, stearic acid or oleic acid.

13. A process for preparing a plate for an assay of a sugar chain-directed antibody which comprises fixing a glycopeptide prepared from tumor cells or serum glycoproteins on a fixing plate by acylation with a higher fatty acid.

14. The process for preparing a plate for an assay of a sugar chain-directed antibody claimed in claim 13, wherein the higher fatty acid is palmitic acid, stearic acid or oleic acid.

15. The process for preparing a plate for an assay of a sugar chain-directed antibody claimed in claim 13, wherein the fixing plate is of synthetic resin, cellulose, glass, wood pieces, textile or paper.

16. The process for preparing a plate for an assay of a sugar chain-directed antibody claimed in claim 15, wherein the synthetic resin is selected from the group consisting of polyethylene, polypropylene, polybutadiene, polystyrene, poly(vinyl chloride), polyacrylonitrile, poly(vinyl alcohol), polyesters, polyamides, polyurethanes, polyethers, and derivatives thereof.

17. The process for preparing a plate for an assay of a sugar chain-directed antibody claimed in claim 15, wherein cellulose is selected from the group consisting of cellulose acetate, ethylcellulose and cellulose nitrate.

* * * * *